United States Patent [19]

Powell et al.

[11] Patent Number: 4,806,694
[45] Date of Patent: Feb. 21, 1989

[54] POLYOLS

[75] Inventors: Richard L. Powell, Tarporley; Brian Young, Winsford, both of England

[73] Assignee: Imperial Chemical Industries PLC, London, England

[21] Appl. No.: 98,970

[22] Filed: Sep. 10, 1987

[30] Foreign Application Priority Data

Sep. 10, 1986 [GB] United Kingdom ............... 8621794

[51] Int. Cl.$^4$ .............................................. C07C 43/11
[52] U.S. Cl. .................... 568/615; 568/842; 568/822; 568/838; 568/839; 568/617; 204/157.9
[58] Field of Search ............... 568/842, 822, 838, 839, 568/615

[56] References Cited

U.S. PATENT DOCUMENTS 2,559,628  7/1951  Joyce ................................. 568/842
3,927,129  12/1975 Hazeldine et al. .................. 568/842

FOREIGN PATENT DOCUMENTS 38-18663  9/1963  Japan ................................. 568/842

Primary Examiner—Howard T. Mars
Attorney, Agent, or Firm—Cushman, Darby & Cushman

[57] ABSTRACT

Fluorine-containing polyols obtained by the free radical addition of a fluoro-olefin having the general formula:

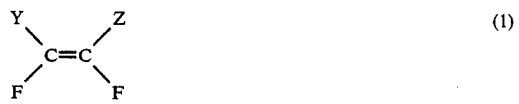

(1)

wherein Y represents F and Z represents Cl or $F(CF_2)n$—wherein n is an integer from 0 to 10 or Y and Z together form a —$(CF_2)m$— chain wherein m represents an integer from 2 to 4 to a polyol wherein each hydroxyl group is directly attached to a group of the formula:

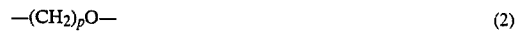

(2)

wherein p is an integer of at least 4.

3 Claims, No Drawings

POLYOLS

This invention relates to polyols and more particularly to fluorine-containing polyols useful as chemical intermediates.

According to the invention, there are provided fluorine-containing polyols obtained by the free radical addition of a fluoro-olefin having the general formula:

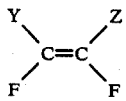
(1)

wherein Y represents F and Z represents Cl or F(CF$_2$)n— wherein n is an integer from 0 to 10 or Y and Z together form a —(CF$_2$)m— chain wherein m represents an integer from 2 to 4 to a polyol wherein each hydroxyl group is directly attached to a group of the formula:

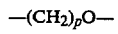
(2)

wherein p is an integer of at least 4.

Fluoro-olefins of formula (1) which may be used in the preparation of the fluorine-containing polyols of the invention include tetrafluoroethene, chlorotetrafluoroethene, hexafluoropropene, perfluorinated nonene-1, hexafluorocyclobutene, octafluorocyclopentene and decafluorocyclohexene.

Examples of polyols wherein each hydroxyl group is directly attached to a group of formula (2) include 1,4-butanediol, 1,6-hexanediol and 1,10-decanediol and polyesters derived therefrom.

Particularly useful polyols for use in making the fluorine-containing polyols of the invention include polytetramethylene glycols such as may be prepared by the polymerisation of tetrahydrofuran in the presence of an acidic catalyst such as boron trifluoride. The polytetramethylene glycols suitably have molecular weights in the range from 162 to 5000.

The free radical addition of the fluoro-olefin to the polyol is performed under conditions in which free radicals are generated. Such conditions have been fully described in the prior art and include the use of known free radical generators, for example azo compounds and the peroxy compounds such as the peroxides, persulphates, percarbonates and perborates as well as ultraviolet and gamma radiation. Di-t-butyl peroxide has been found to be particularly effective.

The free radical addition may be carried out at normal or elevated temperatures, for example temperatures up to 200° C. Solvents are not usually necessary when the polyol is a liquid at the reaction temperature but inert solvents may be used when required. Separation of the reaction product from any remaining starting materials and any solvent used may be effected using conventional techniques.

The fluorine content of the fluorine-containing polyols may be varied by varying the constitution and/or amount of the fluoro-olefin and/or by varying the free radical addition conditions. Typically, the fluorine-containing polyols can have a fluorine content in the range from 5 to 60% on a weight basis although the possibility of lower or higher fluorine contents is not excluded.

The fluorine-containing polyols of the invention may be regarded as polyols having fluorinated side-chains attached to carbon atoms in the polyols. More particularly, the fluorine-containing polyols of the invention may be regarded as polyols having pendent groups of the formula:

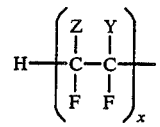
(3)

wherein Y and Z are as defined above and x is a positive integer which must be 1 when Z is Cl or F(CF$_2$)n—.

Products obtained by the addition of the fluoro-olefins to non-polymeric polyols may contain, on average, up to 1 or even more groups of Formula 3 per polyol molecule. Polymeric fluorine-containing polyols, for example polyether polyols, may contain, on average, up to 1 or more groups of Formula 3 per monomer residue.

In general, it is believed that addition of the fluoro-olefin occurs at carbon atoms adjacent to oxygen atoms but the invention is not to be regarded as limited by this or any other theory.

The fluorine-containing polyols of the invention may be used as chemical intermediates in place of or in conjunction with fluorine-free polyols. Furthermore, the fluorine-containing non-polymeric or low molecular weight polyols may be converted by means of known reactions to fluorine-containing polymeric polyols which themselves are useful chemical intermediates. Thus, low molecular weight fluorine-containing polyols may be reacted with dicarboxylic acids or derivatives thereof to form useful polyesters or with alkylene oxides to form useful polyether polyols.

The fluorine-containing polymeric polyols of the invention are particularly valuable for reacting with compounds containing a plurality of groups reactive towards hydroxyl groups to produce useful macromolecular materials which may take the form of elastomers, coatings, soil-, oil- and water repellent textile-finishes, foams or thermoplastics. Examples of such reactive compounds include polyisocyanates, (meth)acrylates and epoxides. In such reactions, the fluorine-containing polymeric polyols of the invention may, if desired, be used in conjunction with conventional fluorine-free polymeric polyols and/or non-polymeric fluorine-containing or fluorine-free polyols. The macromolecular products obtained are characterised by generally superior mechanical properties, reduced water vapour permeability, lower surface free energy and lower surface friction compared with corresponding products obtained from conventional fluorine-free polyols.

Macromolecular materials which may be obtained from the fluorine-containing polyols of the invention include polyurethanes made by reacting the polyols with organic polyisocyanates, the hydroxyl content of the polyols being selected in known manner to provide flexible or rigid products as desired.

Organic polyisocyanates which may be reacted with the fluorine-containing polyols include the aliphatic, cycloaliphatic and aromatic diisocyanates that have been fully described in the polyurethane literature. Suitable aliphatic and cycloaliphatic diisocyanates include hexamethylene, isophorone and 4,4',-dicyclohexylmethane diisocyanates and suitable aromatic diisocyanates include phenylene, 2,4-tolylene, 2,6-tolylene and 4,4'-diphenylmethane diisocyanates. Mixtures of polyisocyanates may be used, for example mixtures of tolylene diisocyanate or diphenylmethane diisocyanate isomers. Other suitable mixtures include the commercial products, commonly known as "crude MDI", containing diphenylmethane diisocyanates together with higher functionality polymethylene polyphenyl polyisocyanates, such mixtures being obtained by the phosgenation of crude aniline-formaldehyde reaction products. If desired, the polyisocyanates may be employed in any of the known modified forms, for example as prepolymers obtained by reaction with fluorine-free or fluorine-containing polyols or as urea-, biuret-, carbodiimide- or uretonimine-modified polyisocyanates. Corresponding polyisothiocyanates could also be used if desired.

In the production of polyurethanes, the fluorine-containing polyols of the invention may be reacted with the polyisocyanates using conventional techniques that have been fully described in the prior art. Depending upon whether the product is to be a homogeneous or microcellular elastomer, a flexible or rigid foam, an adhesive, coating or other form, the reaction mixture may contain other conventional additives, such as chain-extenders, for example 1,4-butanediol or hydrazine, catalysts, for example tertiary amines or tin compounds, surfactants, for example siloxane-oxyalkylene copolymers, blowing agents, for example water and trichlorofluoromethane, cross-linking agents, for example triethanolamine, fillers, pigments, fire-retardants and the like.

Further macromolecular materials which may be obtained from the fluorine-containing polyols of the invention include vinyl type polymers made by polymerising ethylenically unsaturated derivatives of the polyols. Such derivatives may be obtained, for example, by reacting the polyols with ethylenically unsaturated carboxylic acids, for example acrylic, methacrylic and itaconic acids or ester-forming derivatives thereof.

Another useful method of forming ethylenically unsaturated derivatives of the fluorine-containing polyols is to react said polyols with organic polyisocyanates, for example those mentioned above, and then to react the isocyanate group terminated products obtained with hydroxyalkyl acrylates or methacrylates, for example the 2-hydroxyethyl or 2-hydroxypropyl compounds. Alternatively, the fluorine-containing polyols may be reacted with isocyanato-acrylates obtained by reacting a diisocyanate with a hydroxyalkyl acrylate or methacrylate.

The ethylenically unsaturated derivatives of the fluorinated polyols may be polymerised, preferably in the presence of comonomers such as acrylonitrile, styrene, ethyl acrylate, butyl acrylate or methyl methacrylate, using conditions that have been fully described in the prior art for vinyl polymerisations. Useful moulded plastics articles may be made in this way.

Further macromolecular materials which may be obtained from the fluorine-containing polyols of the invention include epoxy resins prepared in conventional manner from epoxy derivatives of the polyols. Such derivatives may be obtained, for example, by reacting the polyols with epichlorohydrin in the presence of bases.

In all of these applications, the fluorine content of the final macromolecular product may be determined by using a fluorine-containing polyol of appropriate fluorine content or by using a mixture of fluorine-containing and fluorine-free polyols.

The invention is illustrated but not limited by the following Examples.

EXAMPLE 1

A 500 ml Hastelloy lined autoclave equipped with "flip-flop" stirrer, pressure gauge, thermocouple pocket, bursting disc and inlet/outlet valve was charged with 175 g molten poly tetrahydrofuran (mol. wt. 650) and 0.7 g di-t-butyl peroxide. The autoclave was then assembled, cooled to $-70°$ C. and evacuated. 175 g HFP (hexafluoropropylene) were vacuum distilled into the autoclave. The autoclave was then heated with stirring to 150° C. (max. pressure reached 650 psig) and stirring continued until no further pressure drop was observed (approx. 1½hr). There was a slight exotherm initially but this was easily controlled.

When no further take up of gas was observed, the autoclave was cooled to room temperature and vented. The product, 330 g colourless viscous liquid, was then heated in a 500 ml round bottomed flask (fitted with thermometer, N2 bleed and splash head connected to 2 drikold traps) to 80° C. @ 10 mm Hg for 2 hrs after which the remaining levels of peroxide and its decomposition products were found to be extremely low by proton nmr.

The product was identified by $^{19}F$ showing the product to contain 37.3% F, which is equivalent to approx. 1 HFP unit grafted on to every other THF unit of the polymer.

A blank run using no initiator was carried out and the very weak $^{19}F$ nmr spectrum of this product suggested that very few of the terminal —OH groups of the polymer had reacted to form ether groups (—OCF$_2$CFHCF$_3$).

The grafting experiments were also carried out on higher molecular weight poly THF (1,000 and 2,000) with similar success.

Other free radical initiators were also tried, but it can be seen from the table below that di-ti-butyl peroxide was by far the most efficient.

| Initiator | Wt. of Initiator | Temp | Time | % F in Product | ≡1 HFP unit every |
|---|---|---|---|---|---|
| di-t-butyl peroxide | 0.7 g | 150° C. | 1½ hrs | 37.3% | 2 units THF |
| di-benzoyl peroxide | 2 g | 80° C. + 100° C. | 2 hrs + 2 hrs | 8.9% | 16 units THF |
| A.D.I.B. | 2 g | 80° C. | 8¾ hrs | 0.7% | 200 units THF |
| di-lauryl peroxide | 3 g | 72° C. | 8 hrs | 13.8% | 9.5 units THF |

EXAMPLE 2

A 500 ml Hastelloy lined autoclave equipped as in Example 1 was charged with 175 g molten polytetrahydrofuran (mol wt 650) and 2.1 g di-t-butyl peroxide. The autoclave was then purged with nitrogen, evacuated, heated to 140° C. and pressurised with HFP to a pressure of 80 psig. As the reaction proceeded (resulting in a pressure drop), the autoclave was repeatedly repressurised with HFP for a period of 1¾ hrs after which the take up of gas was extremely slow. The autoclave was cooled to room temperature and vented and 23 g product was removed for analysis. To the remainder was added a further 2.1 g initiator and the autoclave reassembled. After purging with nitrogen and then HFP, the autoclave was reheated with stirring to 140° C. The autoclave was repeatedly pressurised with HFP as above for a further 1¼ hrs.

On cooling and venting the autoclave, 263 g pale yellow viscous liquid was recovered from the autoclave and was found to contain 31.6% fluorine. The sample removed after 1¾ hrs was found to contain 20.7% fluorine.

EXAMPLE 3

The 500 ml Hastelloy lined autoclave was charged with 175 g poly THF (650) and 0.2 ml di-t-butyl peroxide, purged with nitrogen and evacuated. The autoclave was then heated with stirring to 140° C. and pressurised repeatedly with HFP, as above, until no further take up of gas. A further 0.2 ml initiator was injected into the autoclave and the addition of HFP continued. After a further 7 additions of initiator over a period of 7 hours, the autoclave was cooled to room temperature and vented.

323 g very pale yellow viscous liquid was recovered containing 35.3% fluorine.

EXAMPLE 4

For this experiment a 1 liter autoclave fitted with 4 baffles and a turbine gas entrainment stirrer was used. The autoclave was charged with 350 g poly THF (650) and 1.6 g di-t-butyl peroxide and heated to 140° C. the stirrer speed having been set at 1,000 rpm. HFP was fed in as a gas as in the previous experiment, but at a pressure of 100 psig. After 4 hrs the gas take up was extremely slow and, after cooling to room temperature and venting, by product was removed for analysis —29.1% fluorine.

To the remainder was added a further 1.6 g di-t-butyl peroxide and the autoclave heated with stirring back to 140° C. HFP was fed in for a further 3½ hrs after which the autoclave was again cooled to room temperature and vented.

671 g almost colourless viscous liquid was recovered, which was found to contain 37.7% fluorine.

EXAMPLE 5

A 3.7 liter autoclave (equipped with gas elution stirrer and baffles) was charged with 1225 g poly THF (650) and 7 mls di-t-butyl peroxide. The autoclave was then evacuated and charged with 250 g HFP (by pressurising to 60 psig) and heated with stirring (1,000 rpm) to 140° C. As the reaction proceeded, the autoclave was repeatedly repressurised with HFP at a pressure of 130 psig for 4 hrs. A sample of the product was found to contain 31.5% fluorine.

Following the addition of a further 7 mls peroxide, the reaction was continued for a further 2 hrs after which the fluorine content of the product had increased to 34.5%.

A product containing 41.2% fluorine was obtained after another 7 mls initiator had been added and the reaction continued for a further 2 hours.

EXAMPLE 6

A 500 ml Hastelloy lined autoclave equipped with flip-flop stirrer, pressure gauge, thermocouple, bursting disc and inlet/outlet valve was charged with 175 g molten poly-THF (MW 650) and 2 g di-t-butylperoxide. The autoclave was assembled, purged with nitrogen, cooled to −60 deg C., evacuated and slowly warmed to room temperature. After heating to 106 deg C., it was pressurised to 55 psi with tetrafluoroethylene. When the temperature reached approximately 100 deg C., the pressure started to fall as the reaction commenced. More TFE gas was admitted to the autoclave in portions to maintain the pressure in the range 0 psi to 260 psi and the temperature in the range 134 to 147 deg C. The reaction was exothermic but was controlled by the careful addition of TFE. The addition was continued until the total pressure drop at the reaction temperature was 1505 psi.

The autoclave was cooled to room temperature and vented. The product after degassing was 313.5 g of a milky white viscous liquid. It was identified by F19 NMR which showed that it contained 32% F.

EXAMPLE 7

A 500 ml Hastelloy lined autoclave equipped with flip-flop stirrer, pressure gauge, thermocouple, bursting disc and inlet/outlet valve was charged with 175 g molten poly-THF (MW 650) and 2 g di-t-butylperoxide. The autoclave was assembled, purged with nitrogen, cooled to −60, evacuated, and warmed slowly to room temperature. The autoclave was then heated. When the temperature reached 129 deg C., liquid chlorotrifluoroethene (10 ml) was injected into the autoclave. The reaction was monitored by the fall in pressure. More CTFE liquid was injected into the autoclave in portions to maintain the pressure in the range 130 psi to 255 psi and the temperature in the range 137 to 138 deg C. After 2.25 hours, the pressure ceased dropping indicating that the reaction had finished.

The autoclave was cooled to room temperature and vented. The product after degassing was 194.2 g of a clear colourless viscous liquid. It was identified by F19 NMR which showed that it contained 2% F.

EXAMPLE 8

A 500 ml Hastelloy lined autoclave equipped with flip-flop stirrer, pressure gauge, thermocouple, bursting disc and inlet/outlet valve was charged with 175 g molten poly-THF (MW 650) and 5 g di-t-butylperoxide. The autoclave was assembled, evacuated cooled to −60 deg C. and 137 g of chlorotrifluoroethene vacuum distilled into it. The autoclave was then heated. When the temperature reached about 120 deg C. with a pressure of 460 psi, the pressure started to fall as the reaction commenced. The temperature was maintained in the range 120 to 138 deg C. over 1.67 hours and the pressure fell to 440 psi at 138 deg C. The rate of pressure drop at the end of this period was zero.

The autoclave was cooled to room temperature and vented. The product after degassing was 209.8 g of a clear colourless viscous liquid. From the increase in weight of the product over the poly-THF starting material, it was calculated that the % F in the product was 3%.

We claim:

1. A fluorine-containing polyol obtained by the addition, at a temperature of up to 200° C. and in the presence of a free radical generator, of a fluoro-olefin having the general formula:

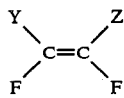

wherein Y represents F and Z represents Cl or $F(CF_2)n-$ wherein n is an integer from 0 to 10 or Y and Z together form a $-(CF_2)m-$ chain wherein m represents an integer from 2 to 4 to a polytetramethylene glycol having a molecular weight in the range from 162 to 5000.

2. A fluorine-containing polyol according to claim 1 wherein the fluoro-olefin is tetrafluoroethene, chlorotetrafluoroethene or hexafluoropropene.

3. A fluorine-containing polyol according to claim 2 having a fluorine content of from 5 to 60% on a weight basis.

* * * * *

UNITED STATES PATENT AND TRADEMARK OFFICE
CERTIFICATE OF CORRECTION

PATENT NO. : 4,806,694

DATED : February 21, 1989

INVENTOR(S) : POWELL et al.

It is certified that error appears in the above-identified patent and that said Letters Patent is hereby corrected as shown below:

Column 1, lines 27 and 28, reads: "chlorotetrafluoroethene"

should read: --chlorotrifluoroethene--.

Column 8, lines 8 and 9, reads: "chlorotetrafluoroethene"

should read: --chlorotrifluoroethene--.

Signed and Sealed this

Thirty-first Day of July, 1990

Attest:

HARRY F. MANBECK, JR.

*Attesting Officer*  *Commissioner of Patents and Trademarks*